United States Patent [19]
Goldblatt et al.

[11] 4,175,546
[45] Nov. 27, 1979

[54] DEVICE FOR MEASURING SENSITIVITY TO VIBRATION

[75] Inventors: Samuel Goldblatt, Amberly Village; Waller M. Scott, Jr., Union Township, Butler County, both of Ohio

[73] Assignee: Ahron P. Leichtman, Amberly, Ohio

[21] Appl. No.: 830,654

[22] Filed: Sep. 6, 1977

[51] Int. Cl.$^2$ ............................................. A61B 10/00
[52] U.S. Cl. ..................... 128/739; 73/663; 310/331
[58] Field of Search ............... 128/2 N, 2 S, 2 T, 2 R; 73/662, 663; 310/331

[56] References Cited
U.S. PATENT DOCUMENTS

| | | | |
|---|---|---|---|
| 2,625,152 | 1/1953 | Frohring | 128/2 N |
| 2,742,035 | 4/1956 | Hancock et al. | 128/2 N |
| 3,336,573 | 8/1967 | Gallaway et al. | 310/331 X |
| 3,497,731 | 2/1970 | Straube | 310/331 X |
| 3,749,948 | 7/1973 | Morris | 310/331 X |

FOREIGN PATENT DOCUMENTS

130621  5/1959  U.S.S.R. ................................. 128/2 R
325966  3/1972  U.S.S.R. ................................. 128/2 S

OTHER PUBLICATIONS

Fucci et al., "New Instrumentation . . . Tongue", The Review of Scientific Instruments, vol. 43, No. 12, pp. 1748-1751, Dec. 1972.

*Primary Examiner*—Lee S. Cohen
*Attorney, Agent, or Firm*—James W. Pearce; Roy F. Schaeperklaus

[57] ABSTRACT

A device for measuring the sensitivity of a patient to externally applied vibration. The device includes a pallometer head which supports a vibratable probe. The probe is caused to vibrate with a selected amplitude and at a selected frequency. The head is supported beneath a table with the probe extending through an opening in the table so that the probe can be engaged by a member of the patient as the member rests on the table. The head is supported on a beam which carries a counterweight so that the probe engages a member of the patient with a controlled pressure.

3 Claims, 13 Drawing Figures

FIG. 5
FIG. 8
FIG. 6
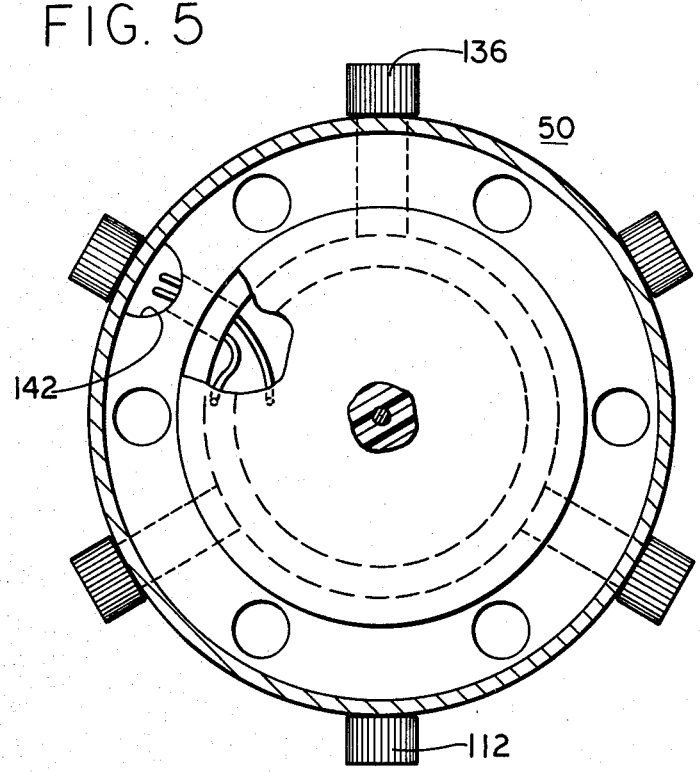
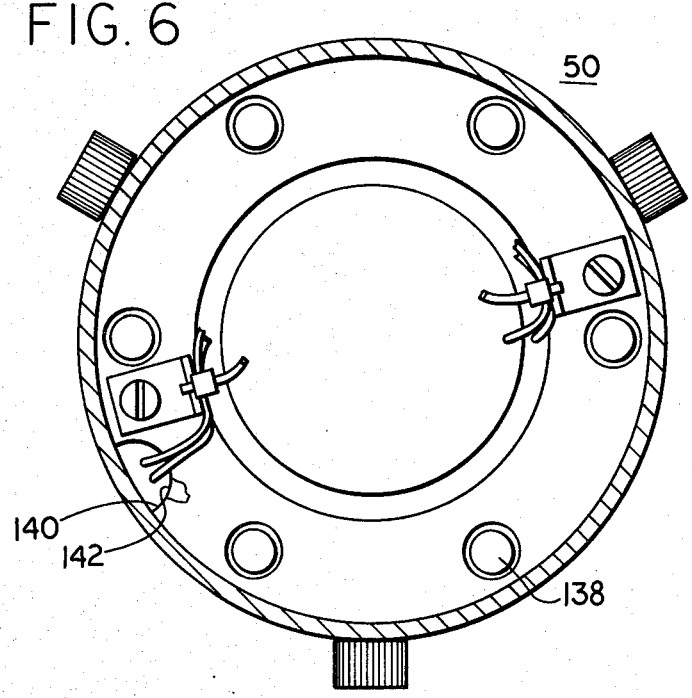
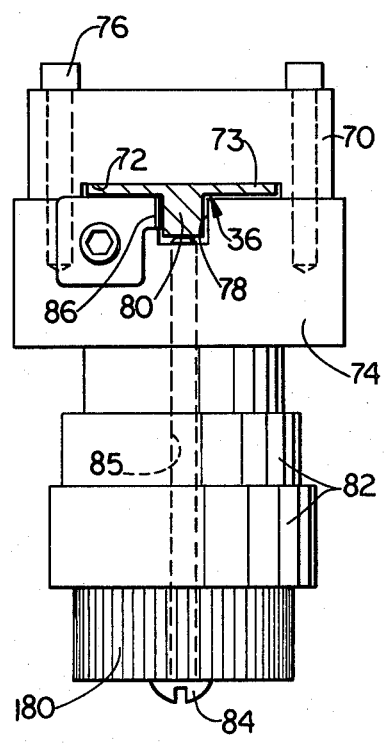

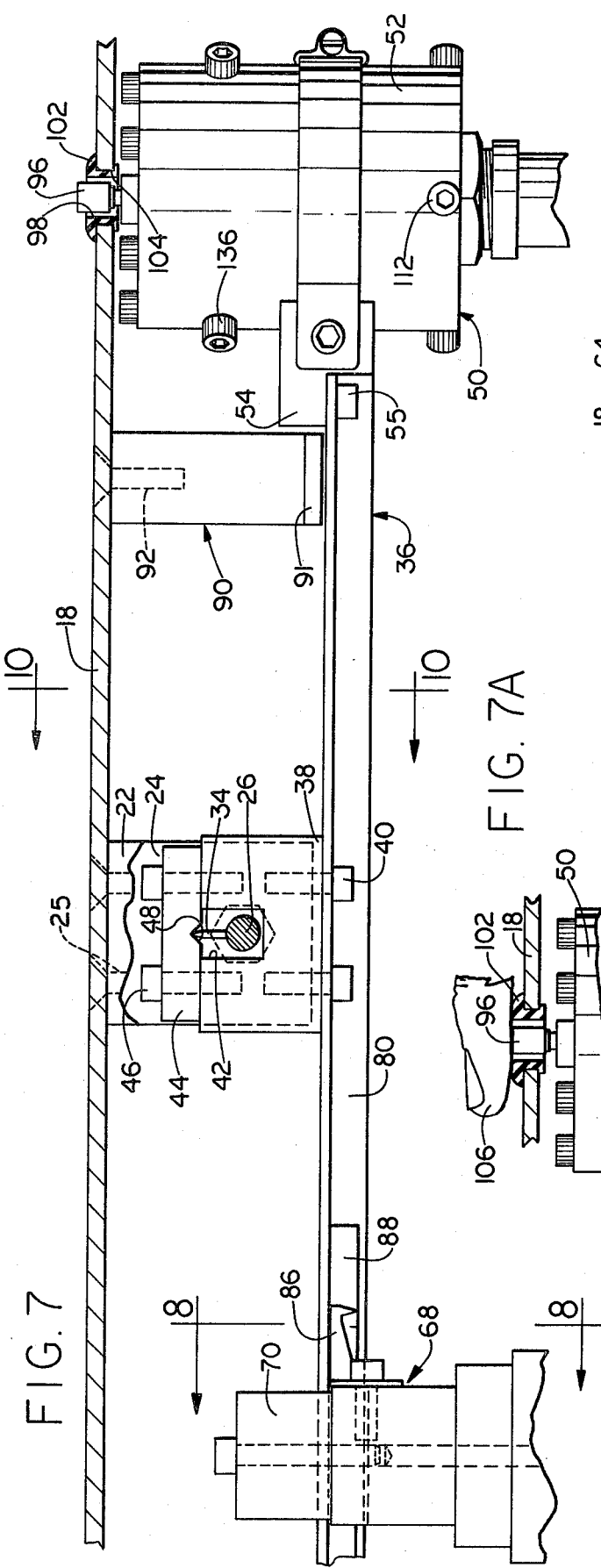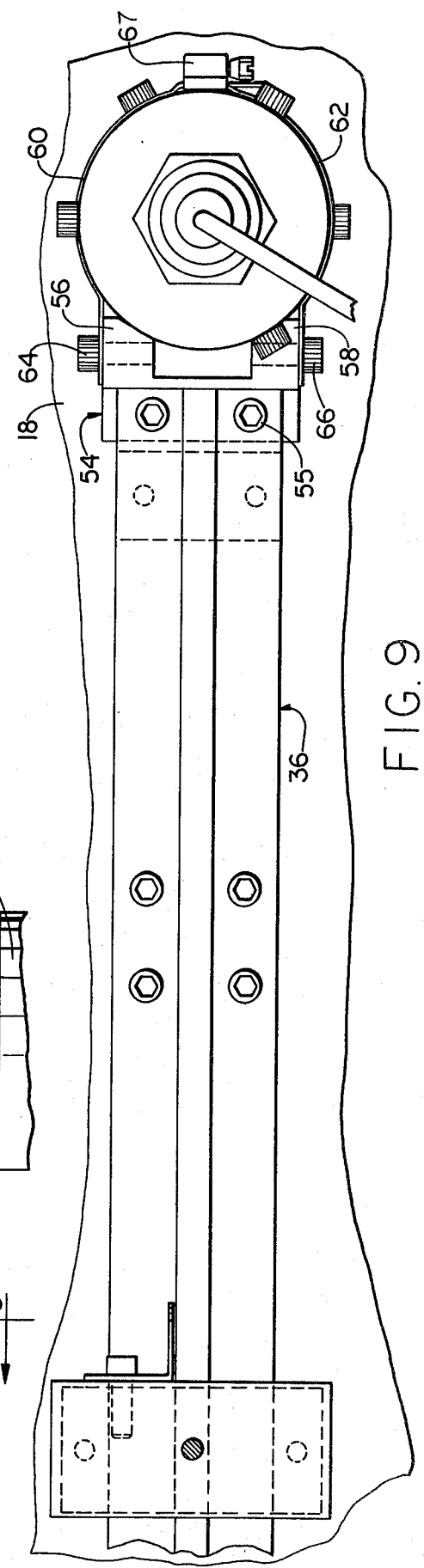

DEVICE FOR MEASURING SENSITIVITY TO VIBRATION

This invention relates to an electronic pallometer or device for testing sensitivity to externally applied vibrations and represents an improvement over the device shown in Hancock, Goldblatt and Mason U.S. Pat. No. 2,742,035.

Human beings suffering from certain pathological conditions have an impaired sensitivity to vibration. The degree of impairment may be measured by the pallometer of our invention and utilized in the diagnosis of such pathological conditions.

Vibration appreciation is depressed in such pathological conditions as diabetes, syphilis, hypothyroidism, leukemia, and many others. As such conditions progress, the depression of vibratory appreciation is a measure of the progress of the disease. On the other hand, when such conditions improve in response to proper treatment, the vibratory appreciation can be improved. The level of improvement in vibratory appreciation can be a measure of the success of treatment.

An object of this invention is to provide a support for a head of a pallometer which permits engagement of a vibrating operative tip thereof by a patient under controlled circumstances so that extraneous influences are minimized.

A further object of this invention is to provide a pallometer support in which the operative tip of the pallometer projects through an opening in a table with other portions of the pallometer being hidden beneath the table.

A further object of this invention is to provide such a pallometer support in which the pallometer head is mounted on a swinging support and in which the support is counterbalanced so that the head of the pallometer is readily displaced when the operative tip is engaged, and the load on the operative tip remains substantially constant.

Briefly, this invention provides a pallometer having a head or tool which is mounted on an end of a balance lever or beam that is supported by a knife edge. The knife edge is mounted beneath a table having an upright opening through which an operative tip of the head projects. A counterweight mounted on the beam urges the head upwardly to lightly engage a stop with the operative tip exposed. When the operative tip is engaged by a patient, the head can swing downwardly so that the pressure of the tip on the patient is constant regardless of the pressure the patient may exert on the table at the edges of the opening.

The above and other objects and features of the invention will be apparent to those skilled in the art to which the invention relates from the following detailed description and the drawings, in which:

FIG. 5 is a view in section taken on the line 5—5 in FIG. 3;

FIG. 6 is a view in section taken on the line 6—6 in FIG. 3;

FIG. 7 is a view partly in side elevation and partly in section showing details of mounting of the pallometer head;

FIG. 7A is a fragmentary view showing the pallometer head in use with a finger engaging a probe tip element thereof;

FIG. 8 is a view in section taken on the line 8—8 in FIG. 7;

FIG. 9 is a view partly in section and partly in bottom plan of the mounting structure shown in FIG. 7;

In the following detailed description and the drawings, like reference characters indicate like parts.

Figure 2:
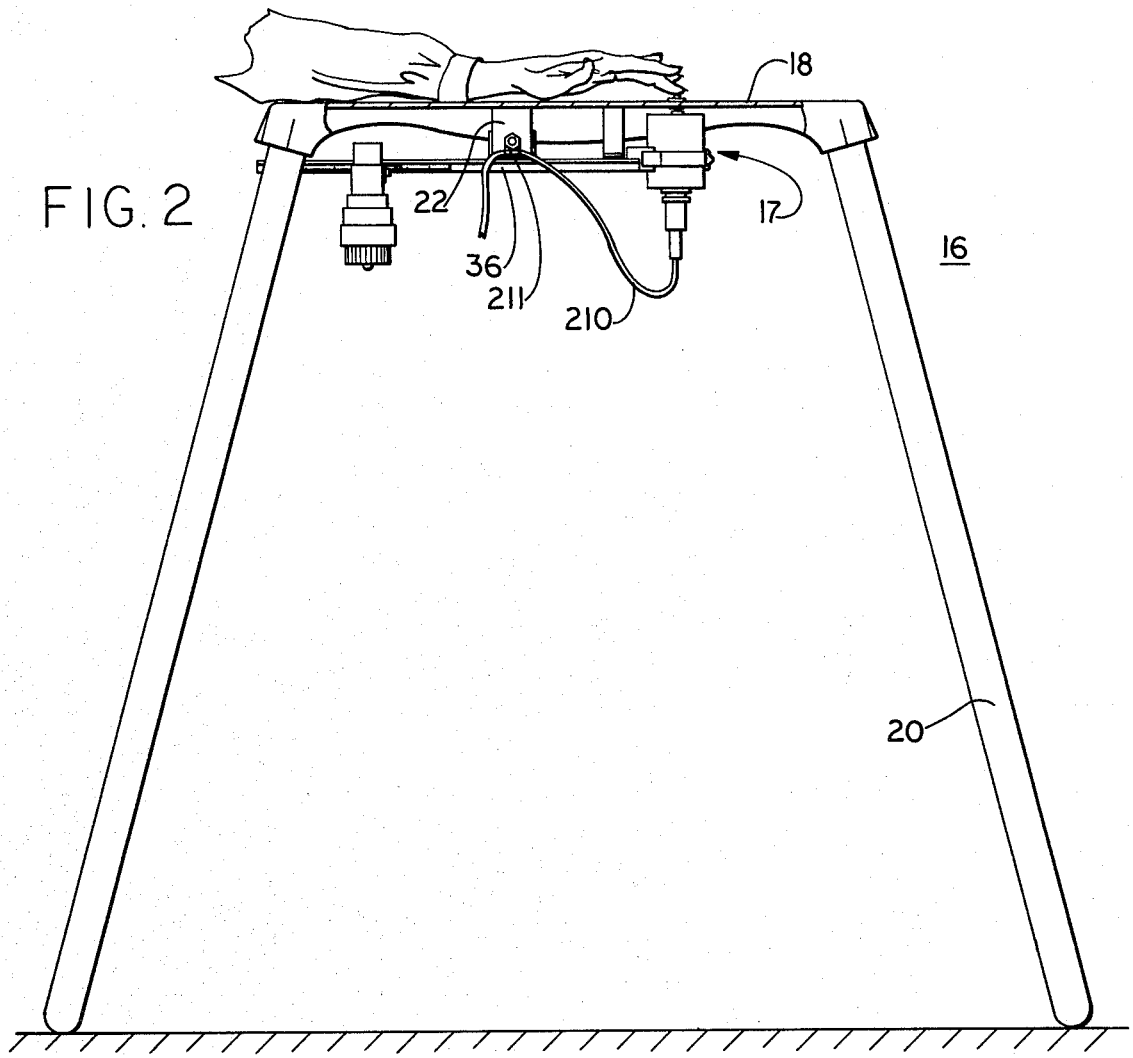
FIG. 2 is a view partly in side elevation and partly in section thereof.
Figure 1:
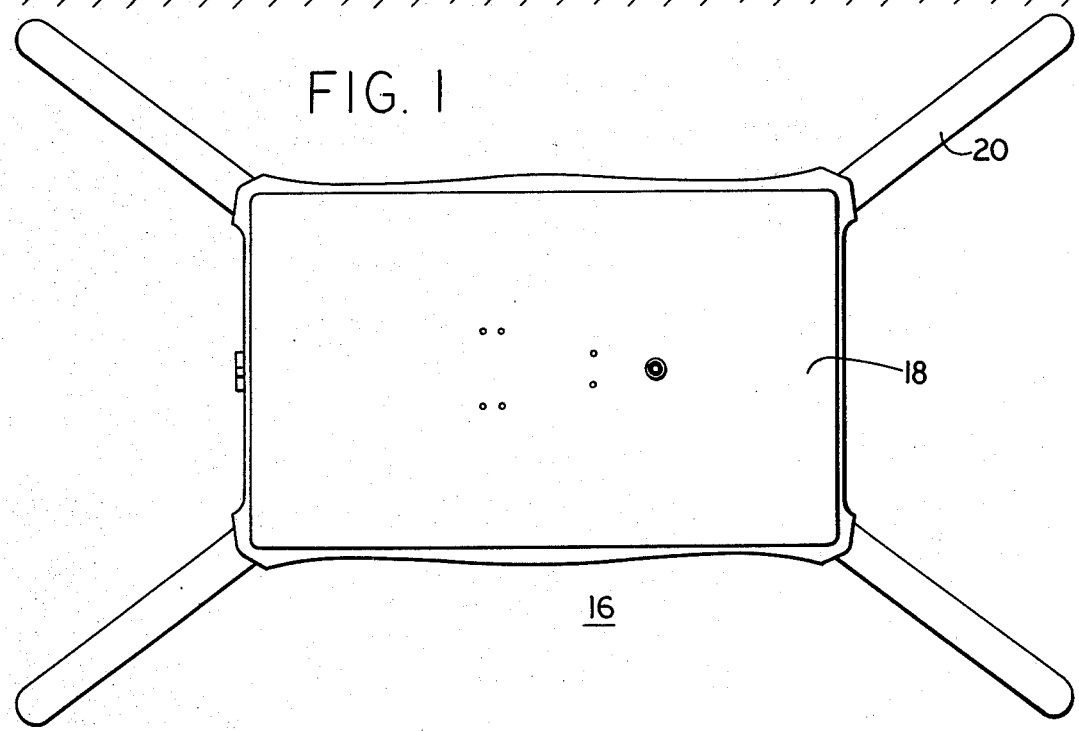
FIG. 1 is a plan view of a pallometer supporting table and pallometer constructed in accordance with an embodiment of this invention.
Figure 10:
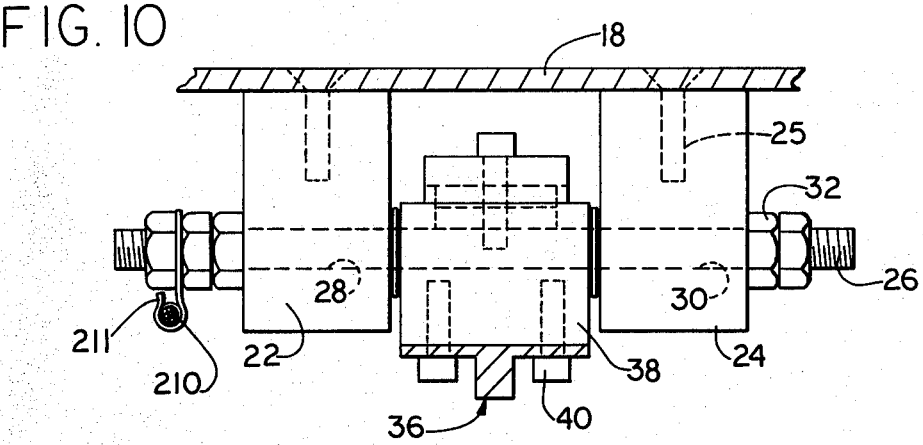
FIG. 10 is a view in section taken on the line 10—10 in FIG. 7.
Figure 11:
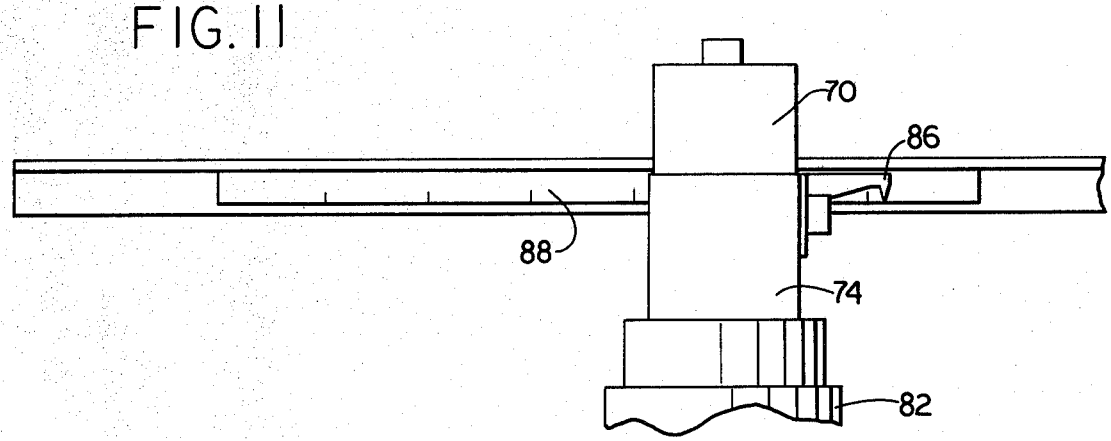
FIG. 11 is a fragmentary view in side elevation of an end portion of a beam and of a counterweight of the structure.

In FIGS. 1 and 2 is shown a table 16 on which is mounted an electronic pallometer 17 constructed in accordance with an embodiment of this invention. The table includes a top 18 supported on legs 20. Pivot supporting blocks 22 and 24 (FIGS. 7 and 10) are attached to the underside of the table top 18 by fasteners 25. A horizontal rod 26 is mounted in transverse bores 28 and 30 in the blocks 22 and 24, respectively. Nuts 32 threaded on end portions of the rod 26 hold the rod 26 in position in the blocks 22 and 24. A knife edge member 34 is mounted on the rod 26 centrally thereof and extends radially upwardly therefrom.

A beam 36 is supported by the knife edge member 34. A block 38 is mounted on the beam 36 by means of fasteners 40. The block 38 is provided with a slot 42, which receives a central portion of the rod 26. A plate 44 is attached to the block 38 overlying the slot 42 by means of fasteners 46. A groove 48 in the underside of the plate 44 receives an upper edge of the knife edge member 34 so that the beam 36 is pivotally mounted under the table top 18.

Figure 3:
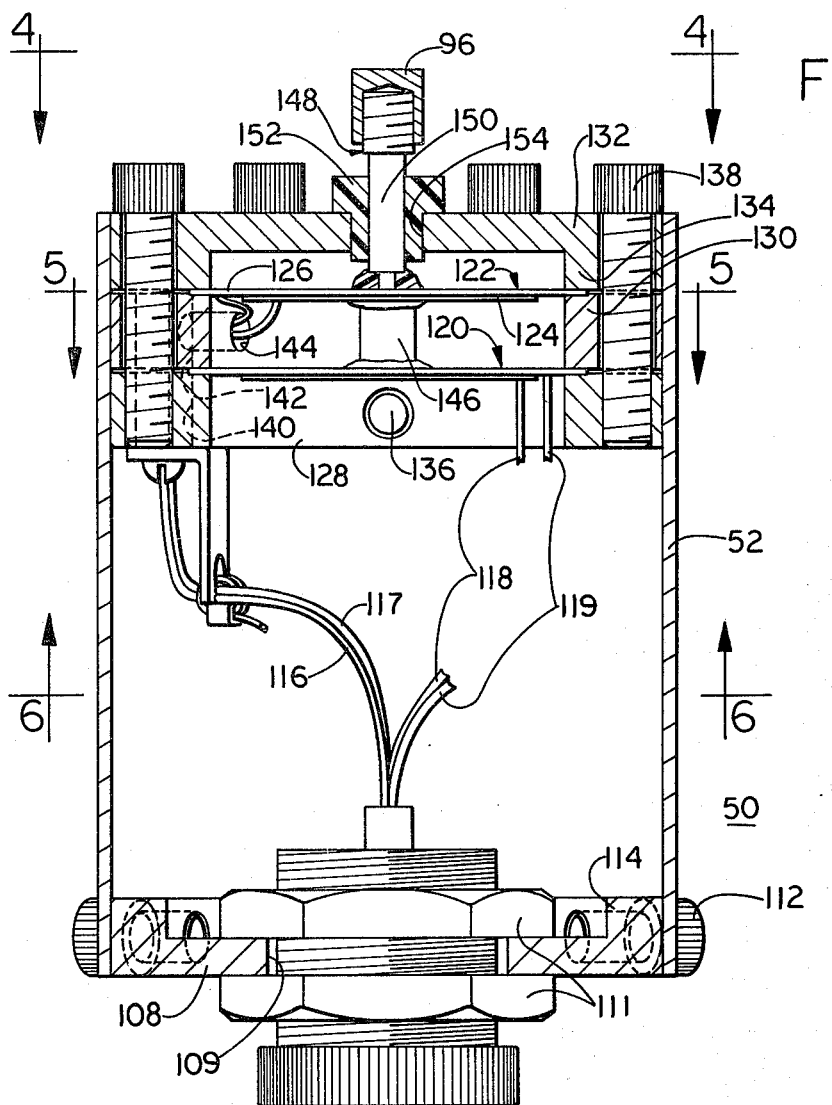
FIG. 3 is a view in upright section on an enlarged scale of a head or tool of the pallometer.
Figure 4:
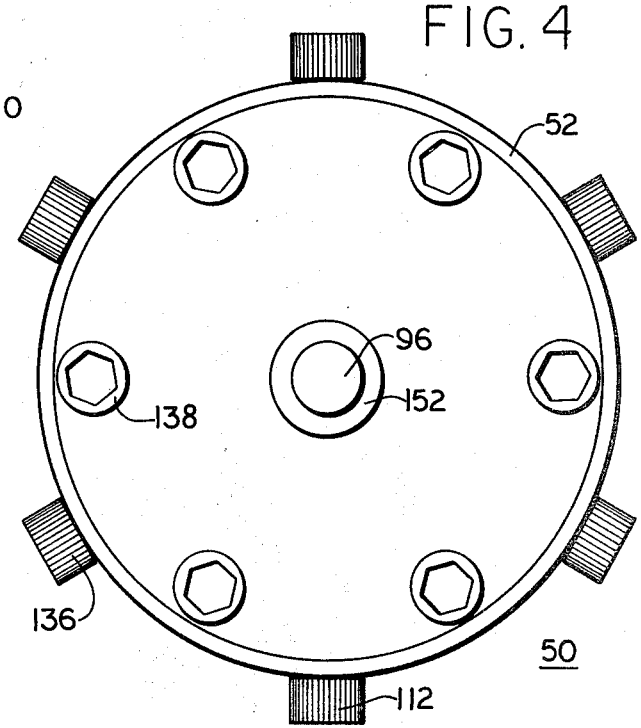
FIG. 4 is a plan view of the head looking in the direction of the arrows 4—4 in FIG. 3.

A pallometer head 50 is mounted at one end of the beam 36. The pallometer head 50 includes a hollow cylindrical body 52 (FIG. 3). A bracket 54 (FIGS. 7 and 9) is attached to the beam 36 at the end thereof by fasteners 55. Arms 56 and 58 of the bracket 54 engage the body 52. Straps 60 and 62 are attached to the arms 56 and 58 by fasteners 64 and 66, respectively. End portions of the straps 60 and 62 are connected by a fastener 67 so that the straps 60 and 62 firmly hold and embrace the body 52 to support the pallometer head 50 on the beam 36.

A counterweight assembly 68 is slidably mounted on the beam 36. The counterweight assembly 68 (FIGS. 7 and 8) includes a slide block 70 provided with a downwardly opening slot 72 in which a main portion 73 of the beam 36 is received. A lower block 74 is attached to the slide block 70 by fasteners 76. A slot 78 in the block 74 receives a rib portion 80 of the beam 36. Weight members 82 are hung on the block 74 by a fastener 84, which is threaded in the block 74 and extends through upright bores 85 in the weight members 82. The fastener 84 is attached to a knurled knob 180. An upper end of the fastener 84 can engage the bottom of the rib portion 80 to lock the counterweight assembly in position on the beam 36. A pointer 86 is attached to the block 74. The pointer 86 cooperates with graduations 88 (FIG. 7)

on the rib portion 80 for indicating the position of the counterweight assembly 68.

A bumper support 90 carries a resilient bumper pad 91 of rubber or other rubber-like material, which limits upward swinging of the pallometer head 50. The bumper support 90 is attached to the underside of the table top 18 by fasteners 92. The resilient bumper pad 91 is adhesively attached to the lower end of the bumper support 90 and is engageable by the beam 36. When the pallometer head 50 is in the raised position of FIG. 7, a probe tip element 96 thereof extends through a central opening 98 in a grommet 102, which is mounted in an opening 104 in the table. The probe tip element can be engaged by finger 106 of a patient as indicated in FIG. 7A, and the pressure of the probe tip element 96 on the finger is determined by the position of the counterweight assembly 68 on the beam 36 (FIG. 7). The grommet 102 can be of rubber or other rubber-like elastomeric material and forms a support for the finger surrounding the probe tip element.

Details of construction of the pallometer head 50 are shown in FIGS. 3, 4, 5 and 6. A lower end of the cylindrical body 52 is closed by a plate 108 having a central opening 109 through which a cable lead-in fitting 110 extends to be held in position therein by nuts 111 threaded thereon. Fasteners 112 threaded in a flange 114 of the plate 108 hold the plate 108 in position. Leads 116, 117, 118 and 119 enter the pallometer head 50 through the cable lead-in fitting 110. A cable 210, through which the leads extend, is supported by a clip 211 (FIGS. 2 and 10) mounted on the rod 26. Two electrical mechanical vibration transducers 120 and 122 are mounted inside the body 52. Each of the transducers includes a disc 124 of piezoelectric ceramic material bonded to an electrically inactive substrate 126, which can be a brass disc. The transducers can each be of the type known as a PZT Unimorph, a trademark of Vernitron Corporation.

The transducers 120 and 122 are held in spaced parallelism by a pair of rings 128 and 130 and a cup-shaped mount member 132. The edge of the brass disc of the transducer 120 is held between the rings 128 and 130. The edge of the brass disc of the transducer 122 is held between the ring 130 and an annular flange 134 of the cup-shaped mount member 132. The ring 128 is held in position in the body 52 by fasteners 136. The ring 130 and the cup-shaped mount member 132 are held in assembled relation with the transducers 120 and 122 and the ring 128 by fasteners 138 threaded in the ring 128. The leads 118 and 119 are connected to the ceramic disc and to the brass disc, respectively, of the transducer 120. The leads 116 and 117 extend through lengthwise slots 140 and 142 in the rings 128 and 130, respectively, and a radial bore 144 in the ring 130 and are attached to the ceramic disc and the brass disc of the transducer 122, respectively.

The transducers 120 and 122 are mechanically connected to vibrate together by a post 146. The post 146 is adhesively attached to the brass disc of the transducer 120 centrally thereof and to the ceramic disc of the transducer 122 centrally thereof. The probe tip element 96 is mounted on a member 148 having a cylindrical body 150, which is slidably mounted in a bushing 152 mounted in a central opening 154 in the cup-shaped mount member 132. The lower end portion of the member 148 is adhesively attached to the brass disc of the transducer 122 centrally thereof. When the transducer 120 is caused to vibrate by electrical components to be discussed hereinafter, the probe tip element 96 and the transducer 122 vibrate therewith.

Figure 12:
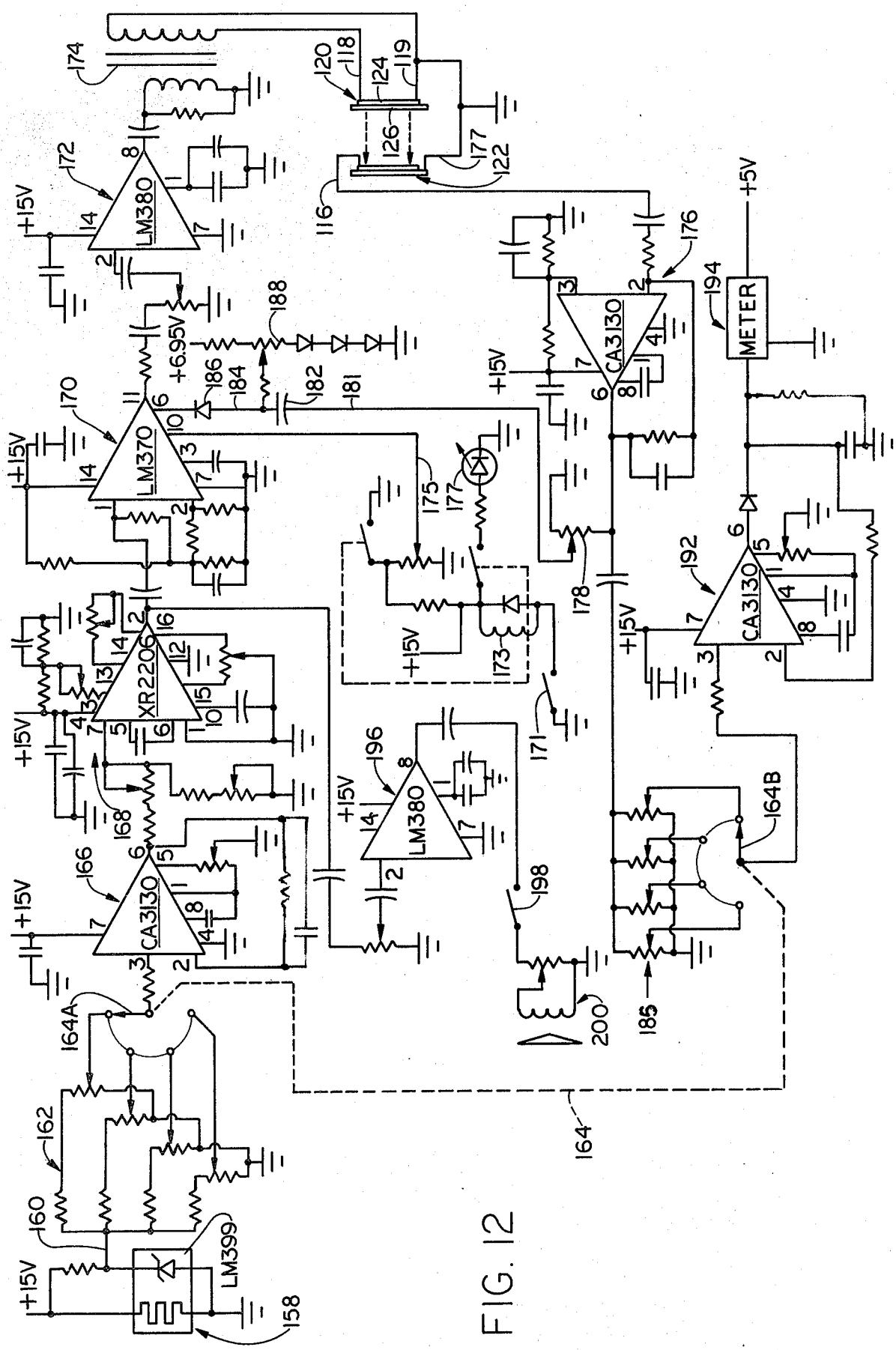
FIG. 12 is a schematic circuit diagram for the pallometer.

The electrical components of the pallometer will now be described with reference to FIG. 12. A voltage stabilizing circuit 158 supplies a constant voltage, which can be +6.95 volts, to a lead 160. The lead 160 is connected to a bank of resistors 162 from which a switch leaf 164A of a selector switch 164 can withdraw a selected voltage. The selected voltage is impressed on a voltage follower stage 166. The output of the voltage follower stage 166 is impressed on a voltage controlled oscillator stage 168. The output of the voltage controlled oscillator stage 168 is coupled to an automatic gain control stage 170. A switch 171 actuates the device. When the switch 171 is closed, it grounds one end of a coil of a relay 173 to actuate the relay. When the relay 173 is actuated, a lead 175 from pin 10 of the automatic gain control stage 170 is grounded to remove attenuation of the automatic gain control stage 170. A light emitting diode 177 indicates the device is actuated. The output of the automatic gain control stage 170 is coupled to a power amplifier stage 172. The power amplifier stage 172 is coupled to a transformer 174, which supplies power to the transducer 120 to cause oscillation of the transducer 122 and of the probe tip element 96 at a frequency determined by the voltage impressed on the voltage controlled oscillator stage 166.

The output of the transducer 122 is coupled to a pickup preamplifier stage 176. The output of the pickup preamplifier stage 176 is connected through a potentiometer 178 to a lead 181. The lead 181 is coupled through a condenser 182 to a lead 184 and through a rectifier 186 to the automatic gain control stage 170. A potentiometer 188, which is connected to the lead 184, can be adjusted to adjust the amplitude of the vibration of the probe tip element 96. The output of the pickup amplifier stage 176 is also coupled through a potentiometer network 185 and a leaf 164B of the selector switch 164 to a peak detector stage 192. The peak detector stage 192 actuates a meter 194, which can be of the type known as a digital voltmeter. The meter 194 registers the amplitude of vibration of the probe tip element 96. The frequency of vibration is controlled by the selector switch 164. The output of the voltage controlled oscillator stage 168 can be coupled to a speaker amplifier stage 196. The speaker amplifier stage 196 supplies power through a speaker on-off switch 198 to a speaker 200, which can provide a tone which masks any tone produced by oscillation of the probe tip element 96.

The mounting arrangement for the pallometer head provides a constant load of the probe tip element 96 on the finger 106 (FIG. 7A) of the patient so that the response of the patient is not altered by varying load, but is determined by the frequency and amplitude of vibration.

The pallometer structure illustrated in the drawings and described above is subject to structural modification without departing from the spirit and scope of the appended claims.

Having described our invention, what we claim as new and desire to secure by Letters Patent is:

1. A device for measuring the sensitivity of a patient to externally applied vibration which comprises a pallometer head, a vibratable probe mounted on the head, means in the head for causing the probe to vibrate with a selected amplitude and at a selected frequency, a table having an opening therein, and means for supporting the head beneath the table with the probe extending through the opening in the table so that the probe can be engaged by a member of the patient as the member rests on the table, the means for supporting the head including a beam, means for attaching the head to the beam, means for pivotally supporting the beam, and counterweight means mounted on the beam to counterbalance the head so that the load of the probe on the member of the patient is constant.

2. A device as in claim 1 in which the counterweight means is movable lengthwise of the beam to selected positions to adjust the load of the probe on the member of the patient.

3. A device as in claim 1 in which a grommet of rubber-like material is mounted in the opening in the table in position for engagement by the member of the patient as the member engages the probe.

* * * * *